US008023714B2

(12) United States Patent
Soenksen

(10) Patent No.: US 8,023,714 B2
(45) Date of Patent: Sep. 20, 2011

(54) SYSTEM AND METHOD FOR ASSESSING IMAGE INTERPRETABILITY IN ANATOMIC PATHOLOGY

(75) Inventor: Dirk G. Soenksen, Carlsbad, CA (US)

(73) Assignee: Aperio Technologies, Inc., Vista, CA (US)

( * ) Notice: Subject to any disclaimer, the term of this patent is extended or adjusted under 35 U.S.C. 154(b) by 1023 days.

(21) Appl. No.: 11/772,748

(22) Filed: Jul. 2, 2007

(65) Prior Publication Data
US 2008/0304722 A1    Dec. 11, 2008

Related U.S. Application Data

(60) Provisional application No. 60/942,390, filed on Jun. 6, 2007.

(51) Int. Cl.
*G06K 9/00* (2006.01)
(52) U.S. Cl. ...................................................... 382/132
(58) Field of Classification Search .................. 382/112, 382/128, 132; 378/21; 702/82, 84
See application file for complete search history.

(56) References Cited

U.S. PATENT DOCUMENTS

| | | | |
|---|---|---|---|
| 6,065,119 A * | 5/2000 | Sandford et al. ................ 726/22 |
| 6,278,793 B1 * | 8/2001 | Gur et al. ....................... 382/128 |
| 7,106,891 B2 | 9/2006 | Wyman et al. | |
| 7,133,545 B2 | 11/2006 | Douglass et al. | |
| 7,190,818 B2 | 3/2007 | Ellis et al. | |
| 7,376,258 B2 * | 5/2008 | Klein et al. ..................... 382/137 |
| 2005/0123181 A1 * | 6/2005 | Freund et al. .................. 382/128 |
| 2005/0256743 A1 * | 11/2005 | Dale ................................... 705/2 |
| 2006/0159325 A1 * | 7/2006 | Zeineh et al. ................... 382/128 |
| 2006/0159367 A1 * | 7/2006 | Zeineh et al. ................... 382/276 |
| 2007/0012886 A1 * | 1/2007 | Tearney et al. ............... 250/459.1 |
| 2007/0172100 A1 * | 7/2007 | Lefebvre ........................ 382/128 |
| 2009/0290768 A1 * | 11/2009 | De La Torre-Bueno ...... 382/128 |

OTHER PUBLICATIONS

Imagery Resolution Assessments and Reporting Standards (IRARS) Committee, Civil NIIRS Reference Guide, Mar. 1996.
International Search Report and Written Opinion for PCT/US2008/066125 dated Sep. 26, 2008.

* cited by examiner

*Primary Examiner* — Jason M Repko
*Assistant Examiner* — Shervin Nakhjavan
(74) *Attorney, Agent, or Firm* — Pattric J. Rawlins; Procopio Cory Hargreaves & Savitch LLP

(57) ABSTRACT

A portion of imagery data is obtained from a digital slide and a protocol of image analysis/diagnostic tasks is performed on the portion of imagery data by a pathologist or an image analysis module. The result of each task (e.g., success or no success) is recorded and a score is determined for the portion of the imagery data. Multiple portions of imagery data from the digital slide are analyzed and scored and the various scores from the multiple portions of imagery data are calculated to determine an overall score for the digital slide. Regions of the digital slide can be scored separately. Multiple rounds of scoring (by different pathologists and/or different image analysis algorithms) may be employed to increase the accuracy of the score for a digital slide or region thereof.

19 Claims, 7 Drawing Sheets

| No | Tasks |
|---|---|
| 1 | Task 1 |
| 2 | Task 2 |
| 3 | Task 3 |
| 4 | Task 4 |
| ... | ... |
| N-2 | Task N-2 |
| N-1 | Task N-1 |
| N | Task N |

Figure 6

| Image Quality Rating | Tasks |
|---|---|
| 0 (Lowest Image Quality) | |
| 1 | |
| 2 | |
| 3 | |
| 4 | |
| 5 | |
| 6 | |
| 7 | |
| 8 | |
| 9 (Highest Image Quality) | |

Figure 7

| No | Tasks | Scores on Image Quality A | | | | | | | | | | % Yes |
|---|---|---|---|---|---|---|---|---|---|---|---|---|
| | | 1 | 2 | 3 | 4 | 5 | 6 | 7 | 8 | 9 | 10 | |
| 1 | Task 1 | Y | N | Y | Y | Y | N | N | N | Y | Y | 60% |
| 2 | Task 2 | Y | Y | Y | Y | N | Y | Y | Y | N | Y | 80% |
| 3 | Task 3 | Y | Y | Y | N | Y | N | Y | N | N | Y | 60% |
| 4 | Task 4 | Y | N | Y | Y | Y | Y | Y | Y | Y | Y | 90% |
| ... | ... | ... | ... | ... | ... | ... | ... | ... | ... | ... | ... | ... |
| N-2 | Task N-2 | N | Y | Y | Y | N | Y | Y | Y | Y | Y | 80% |
| N-1 | Task N-1 | N | Y | Y | Y | Y | Y | Y | N | N | Y | 70% |
| N | Task N | Y | Y | Y | Y | Y | Y | Y | Y | Y | N | 90% |

Figure 8

| No | Tasks | Scores on Image Quality B | | | | | | | | | | % Yes |
|---|---|---|---|---|---|---|---|---|---|---|---|---|
| | | 1 | 2 | 3 | 4 | 5 | 6 | 7 | 8 | 9 | 10 | |
| 1 | Task 1 | N | N | Y | Y | Y | N | N | N | N | Y | 40% |
| 2 | Task 2 | Y | N | Y | Y | N | Y | Y | Y | N | Y | 70% |
| 3 | Task 3 | Y | Y | N | N | Y | N | Y | N | N | Y | 50% |
| 4 | Task 4 | Y | Y | Y | Y | N | Y | Y | Y | Y | N | 80% |
| ... | ... | ... | ... | ... | ... | ... | ... | ... | ... | ... | ... | ... |
| N-2 | Task N-2 | N | Y | N | Y | N | Y | Y | Y | N | Y | 60% |
| N-1 | Task N-1 | N | Y | Y | N | Y | Y | Y | N | N | Y | 60% |
| N | Task N | Y | N | Y | Y | Y | Y | Y | Y | Y | Y | 90% |

Figure 9

| No | Tasks | Scores on Image Quality C |   |   |   |   |   |   |   |   |   | % Yes |
|---|---|---|---|---|---|---|---|---|---|---|---|---|
|   |   | 1 | 2 | 3 | 4 | 5 | 6 | 7 | 8 | 9 | 10 |   |
| 1 | Task 1 | N | N | Y | Y | Y | N | N | N | N | Y | 40% |
| 2 | Task 2 | Y | N | Y | Y | N | Y | N | Y | N | Y | 60% |
| 3 | Task 3 | Y | N | N | N | Y | N | Y | N | N | Y | 40% |
| 4 | Task 4 | Y | Y | N | Y | N | Y | Y | Y | Y | N | 70% |
| ... | ... | ... | ... | ... | ... | ... | ... | ... | ... | ... | ... | ... |
| N-2 | Task N-2 | N | Y | N | N | N | N | Y | N | N | Y | 30% |
| N-1 | Task N-1 | N | Y | Y | N | Y | N | Y | N | N | Y | 50% |
| N | Task N | Y | N | Y | Y | Y | N | Y | Y | Y | Y | 80% |

Figure 10

| No | Tasks | Scores on Image Quality D |   |   |   |   |   |   |   |   |   | % Yes |
|---|---|---|---|---|---|---|---|---|---|---|---|---|
|   |   | 1 | 2 | 3 | 4 | 5 | 6 | 7 | 8 | 9 | 10 |   |
| 1 | Task 1 | N | N | N | N | Y | N | N | N | N | Y | 20% |
| 2 | Task 2 | Y | N | N | Y | N | N | N | Y | N | N | 30% |
| 3 | Task 3 | N | N | N | N | Y | N | N | N | N | N | 10% |
| 4 | Task 4 | Y | N | N | Y | N | Y | Y | N | Y | N | 50% |
| ... | ... | ... | ... | ... | ... | ... | ... | ... | ... | ... | ... | ... |
| N-2 | Task N-2 | N | Y | N | N | N | N | N | N | N | Y | 20% |
| N-1 | Task N-1 | N | Y | N | N | Y | N | Y | N | N | N | 30% |
| N | Task N | Y | N | Y | N | Y | N | Y | Y | Y | Y | 70% |

Figure 11

| No | Tasks | Image Quality (A=Highest, D=Lowest) | | | |
|---|---|---|---|---|---|
| | | A | B | C | D |
| 1 | Task 1 | 60% | 40% | 40% | 20% |
| 2 | Task 2 | 80% | 70% | 60% | 30% |
| 3 | Task 3 | 60% | 50% | 40% | 10% |
| 4 | Task 4 | 90% | 80% | 70% | 50% |
| ... | ... | ... | ... | ... | ... |
| N-2 | Task N-2 | 80% | 60% | 30% | 20% |
| N-1 | Task N-1 | 70% | 60% | 50% | 30% |
| N | Task N | 90% | 90% | 80% | 70% |

Figure 12

| | Image Quality (A=Highest, D=Lowest) | | | |
|---|---|---|---|---|
| | A | B | C | D |
| Least Challenging Tasks | Task 4 (90%) | Task N (90%) | Task N (80%) | Task N (70%) |
| | Task N (90%) | Task 4 (80%) | Task 4 (70%) | Task 4 (50%) |
| | Task 2 (80%) | Task 2 (70%) | Task 2 (60%) | Task 2 (30%) |
| | Task N-2 (80%) | Task N-2 60%) | Task N-2 30%) | Task N-2 20%) |
| | Task N-1 (70%) | Task N-1 (60%) | Task N-1 (50%) | Task N-1 (30%) |
| Most Challenging Tasks | Task 1 (60%) | Task 1 (40%) | Task 1 (40%) | Task 1 (20%) |

Figure 13

| Image Quality Rating | Tasks |
| --- | --- |
| 0 (Lowest Image Quality) | Task 4 |
| 1 | Task N |
| 2 | Task 2 |
| 3 | |
| 4 | |
| 5 | |
| 6 | |
| 7 | Task N-2 |
| 8 | Task N-1 |
| 9 (Highest Image Quality) | Task 1 |

SYSTEM AND METHOD FOR ASSESSING IMAGE INTERPRETABILITY IN ANATOMIC PATHOLOGY

RELATED APPLICATION

The present application claims priority to U.S. provisional patent application Ser. No. 60/942,390 filed on Jun. 6, 2007, which is incorporated herein by reference in its entirety.

BACKGROUND

1. Field of the Invention

The present invention generally relates to the field of digital pathology and more specifically relates to systems and methods for determining the quality of and/or assessing the interpretability of digital slide images.

2. Related Art

While scientific measures such as modulation transfer function ("MTF"), resolution and the signal to noise ratio ("SNR") can be used to objectively quantify image capture devices, it is relatively difficult to objectively assess the quality or interpretability of the imagery data that is generated by such devices, particularly when the imagery data is destined to be subjectively examined by a human, for example in the evaluation of digital slide images in pathology.

Furthermore, the challenges associated with assessing image quality and/or interpretability are exacerbated for digital slide images that are read by pathologists because digital slides are extraordinarily large, typically multiple gigabytes in size. This significant amount of imagery data makes it very difficult to examine every area of a digital slide at full resolution to determine its quality and/or interpretability. Additionally, the patterns (i.e., the features and clues) that pathologists look for when making a diagnosis vary between tissue types and this is further confounded because there is no formal agreement among pathologists about the criteria and tasks used to make diagnoses of specific tissue types. Therefore, what is needed is a system and method that provides an objective way to assess the quality and/or interpretability of a digital slide image to overcome these significant problems as described above.

SUMMARY

Described herein are systems and a methods for objectively assessing the quality and/or interpretability of a digital image that can be used in digital pathology to compare imagery data from different image capture devices, define the level of image quality or interpretability required to accomplish specific diagnostic or interpretative tasks, and provide a basis for automating the assessment of image quality or interpretability. A significant advantage of the described systems and methods is that they provide a pathologist or clinician the ability to determine whether the image quality of a digital slide is sufficient to complete certain types of diagnostic or interpretative tasks.

The system employs a rating scale for image interpretability in anatomic pathology. The rating scale is independent of any particular image capture device and is used to objectively measure the image quality or interpretability of any image type, for example images from a camera on a microscope or from a high resolution slide scanner. The rating scale is based on diagnostic tasks and criteria that are meaningful to pathologists and clinicians and can be applied to any tissue type or stain or any combination of tissue type and stain, including for example, hematoxilin and eosin ("H&E"), immunohistochemical ("IHC") stains, and special stains.

A portion of imagery data is obtained from a digital slide and the protocol of tasks is performed on the portion of imagery data by a pathologist or an image analysis module. The result of each task (e.g., success or no success) is then recorded and a score is determined for the portion of the imagery data. More imagery data from the digital slide may be subsequently analyzed until a sufficient amount of imagery data from the digital slide has been analyzed to accurately score the entire digital slide. The various scores from the various portions of imagery data can then be combined to determine an overall score for the digital slide. Portions of the digital slide may be scored separately. Additionally, multiple rounds of scoring (by different pathologists or different image analysis algorithms) may also be employed to increase the accuracy of the score for a digital slide. Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 6 is a block diagram illustrating an example image interpretability task list according to an embodiment of the present invention;

FIG. 7 is a block diagram illustrating an example image interpretability rating scale according to an embodiment of the present invention;

FIGS. 8-11 are block diagrams illustrating example image interpretability scores according to an embodiment of the present invention;

FIG. 12 is a block diagram illustrating an example image interpretability scoring summary according to an embodiment of the present invention;

FIG. 13 is a block diagram illustrating an example image interpretability task ranking according to an embodiment of the present invention;

DETAILED DESCRIPTION

Certain embodiments as disclosed herein provide for systems and methods for assessing image interpretability in anatomic pathology. For example, one method as disclosed herein allows for an image server to obtain a portion of imagery data from a digital slide and record scores for various diagnostic tasks that are performed on the portion of imagery data. Aggregate scores for a plurality of portions of imagery data are then calculated to determine an overall image interpretability score for the digital slide or a portion thereof.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figure 1:
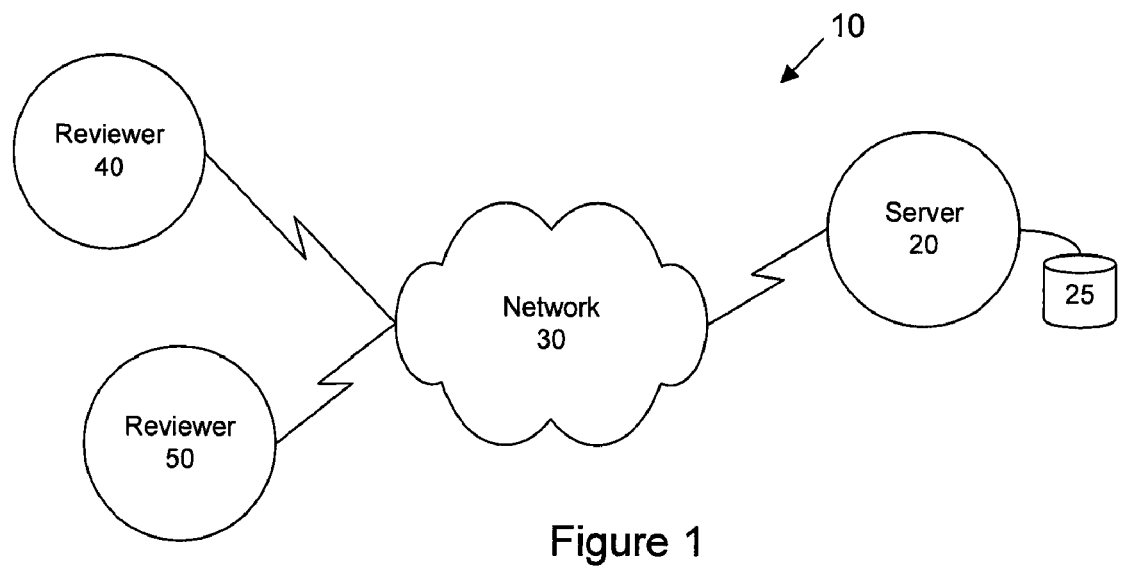
FIG. 1 is a network diagram illustrating an example system for image interpretability assessment according to an embodiment of the present invention.

FIG. 1 is a network diagram illustrating an example system 10 for image interpretability assessment according to an embodiment of the present invention. In the illustrated embodiment, the system 10 comprises an image server 20 that is communicatively coupled with reviewer device 40 and reviewer device 50 via a network 30. The image server 20 is configured with a data storage area 25.

The image server 20 can be implemented using a conventional computer device and is configured to maintain in the data storage area 25 a plurality of digital slide images, for example digital images of physical tissue samples on microscope slides. These digital slides can be in any of a variety of image formats and data formats. The server also maintains in data storage area 25 various program modules that can be used to facilitate and implement the functions for assessing image interpretability. For example, modules for obtaining portions of digital slide imagery data, modules for executing image analysis algorithms on portions of digital slide imagery data, and other modules can be maintained by the image server 20 in data storage area 25.

The data storage area 25 can be any sort of internal or external memory device and may include both persistent and volatile memories. The function of the data storage area 25 is to maintain data (e.g., image data and operational modules) for long term storage and also to provide efficient and fast access to instructions for applications that are executed by the server 20.

The server 20 and the reviewers 40 and 50 are all communicatively coupled with the network 30. The network 30 is configured for data communications (e.g., between server 20 and reviewer 40) over a wide geographical area and can be communicatively coupled with one or more public or private networks (not shown), which may include that particular aggregation of networks commonly known as the Internet.

The reviewers 40 and 50 can also be implemented using a conventional computer device or other communication device with the ability to connect to the network 30. For example, the reviewers 40 and 50 can include any of a variety of communication devices including a wireless communication device, personal digital assistant ("PDA"), personal computer ("PC"), laptop computer, PC card, special purpose equipment, or any combination of these and other devices capable of establishing a communication link over network 30 with the server 20. The reviewers 40 and 50 may be configured with data storage areas (not shown) and their primary function is to present digital slide information to an analyst (e.g., a pathologist or technician) and pass input from the analyst to the server 20.

Figure 2:
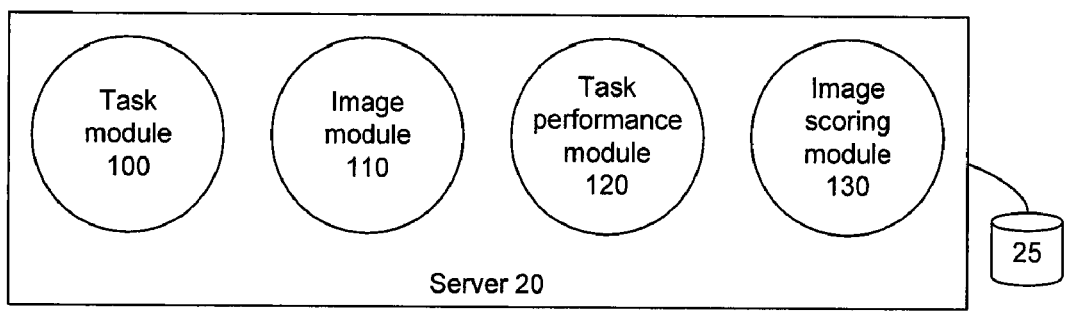
FIG. 2 is block diagram illustrating an example server for image interpretability assessment according to an embodiment of the present invention.

FIG. 2 is a block diagram illustrating an example server 20 for image interpretability assessment according to an embodiment of the present invention. In the illustrated embodiment, the server 20 comprises a task module 100, an image module 110, a task performance module 120, and an image scoring module 130. The server 20 is again configured with a data storage area 25 as described above.

The task module 100 is employed to create and maintain one or more sets of tasks. The sets of tasks can be tissue type specific, for example a first set of tasks may be required for analysis of a tissue sample, while a second set of tasks may be required for analysis of a blood sample. In certain cases, individual tasks within the various sets of tasks may overlap. The sets of tasks may be established by a standards body or other similar group and an individual task, for example, may include the diagnostic tasks and criteria that would be performed using conventional microscopy by a board-certified pathologist who is familiar with the particular tissue type and stain that appears in the digital slide image.

Because a digital slide provides instant access to many intermediate image resolution levels—from thumbnail image (lowest resolution image) to full-resolution baseline image (highest resolution quality)—a more meaningful rating scale is created by selecting tasks that can be accomplished at high image resolution, e.g., using a microscope at high power (for example, with a 40×/0.75 objective lens). The selection of criteria and tasks is tissue-specific and including tasks that can be accomplished at lower image resolutions may be appropriate for some tissue types (e.g., dermatopathology). By comparison, an image interpretabilty rating scale aimed at hematopatholgy specimens, should reflect criteria and tasks that correspond to oil-immersion resolutions; for example using a 100×/1.4 objective lens. In general, higher resolution images have higher image quality when focus and illumination and other image capture attributes are relatively equal.

A list of potential tasks and criteria is provided in the table below for a prostate cancer specimen:

1. Identify areas of overlapping cores
2. Identify red blood cells in vessels
3. Identify corpora amylacea
4. Distinguish between a Gleason grade 3 and Gleason grade 5 pattern
5. Distinguish between nerve tissue and stroma
6. Identify individual muscle bundles
7. Detect the "pink-colored" secretions of normal prostate glands
8. Detect the presence of the "amphophilic cytoplasm" of malignant prostate glands
9. Identify the basal layer of a prostate gland
10. Detect the presence of nucleoli
11. Count the number of nuclei within a gland
12. Detect the borders of luminal cells
13. Detect the presence of "blue-tinged mucus
14. Detect the presence of mitotic figures
15. Count the number of endothelial nuclei within a vessel
16. Detect the presence of lipofuschin/pigment
17. Approximate the diameter of a nucleus to within 2 μm
18. Detect clear cut nuclear envelope borders
19. Identify individual nerve fibers
20. Detect the concavity of individual red blood cells
21. Identify the individual lobes of a neutrophils
22. Identify individual striations in muscle fibers
23. Distinguish between the nucleus of stromal fibroblast and a lymphocyte
24. Distinguish between "normal" and "abnormal" mitotic figures
25. Identify individual nucleoli within a multi-nucleolated cell In one embodiment, the criteria and tasks for specific tissue types are established by consensus among pathologists, with some criteria being common among different tissue types. These criteria are then provided to the task module 100 and stored in the data storage area 25. While some pathologists may disagree about including or excluding certain tasks or criteria, organizations like the College of American Pathologists ("CAP") may advantageously publish and standardize the generally accepted tasks and criteria for different tissue types.

The image module 110 is configured to obtain imagery data from a digital slide. The digital slide may be stored locally or remotely and may be accessed through a separate database or be integrated with a database under the operation of the image module 110. Starting from scratch, the image module may facilitate the scanning of a glass slide to create a digital slide image at the required resolution for accomplishing the criteria and tasks for the particular tissue type. Alternatively, the image module 110 may obtain imagery data at the required resolution via a network server, remote storage area, or local data storage area 25. In one embodiment using prostate cancer biopsies, the required scanning resolution is achieved by use of a 40×/0.75 objective lens, which corresponds to a 0.25 µm per pixel scanning resolution.

The task performance module 120 is configured to manage the performance of the various tasks that are required in the set of tasks for the particular tissue type. In one embodiment, the task performance module provides portions of imagery data from the digital slide image to the display screen of a reviewer device so that an analyst (e.g., a technician or pathologist) may analyze the portions of imagery data to perform each task in the set of tasks corresponding to the particular tissue type. The task performance module 120 also records the success or failure of the analyst in performing the task. This may be accomplished by presenting a dialogue box to the analyst with a binary input capability that allows the analyst to register whether the task was successfully performed or not successfully performed.

Alternatively, or in combination, the task performance module may employ one or more computer implemented image processing algorithms that are capable of analyzing imagery data from a digital slide to perform a particular task. For example, an image processing algorithm capable of counting the number of cells in a specimen may be used to determine whether there is sufficient contrast and resolution in the imagery data to separately identify individual cells. Thus, successfully being able to count the number of cells in a tissue sample may result in the task performance module 120 recording as successful the task for being able to separately identify individual cells. Advantageously, as more sophisticated and robust image processing algorithms are developed, fewer tasks may need to be performed by analysts, thus decreasing the time to score digital slide images and improving the reliability of predictable and repeatable scoring through elimination of the human element.

In one embodiment, the task performance module 120 measures an analyst's ability to perform each of the diagnostic tasks and criteria in the task list on representative portions of imagery data from a digital slide. This is accomplished by the task performance module 120 by selecting random portions of imagery data from the digital slide (so as to be representative of the entire area of the digital slide) or alternatively by selecting portions of imagery data from meaningful regions of the slide, which can be identified using a microscope (e.g., manually) or image processing algorithm (e.g., computer aided/automatically).

Notably, one goal of the image interpretability scale is to rank-order the diagnostic tasks and criteria based on the interpretability of the digital slide imagery. Accordingly, the selected fields of view (selected randomly or otherwise) preferably correspond to different image qualities, otherwise the scale will not have sufficient dynamic range and it will not be possible to differentiate the relative difficulty of achieving the criteria and tasks. In one embodiment, different image qualities for the same portion of a digital slide image can be obtained, for example, by sub-sampling the imagery data, by compressing the imagery data (and further by changing the quality factor during image compression), by scanning the glass slide at different resolutions, any by other means for simulating different image qualities.

The image scoring module 130 is configured to calculate, based on the success or failure of task performance, an image interpretability score. The score is calculated for each portion of a digital slide image that is examined by an analyst (or image processing algorithm). A separate score may also be calculated for various regions of a digital slide and a further separate score may be calculated for the entire digital slide. In one embodiment, entire digital slide scores are calculated from the respective scores of individual portions of imagery data, or from the respective scores of individual regions of imagery data (comprising a plurality of portions), or from a combination of individual portions and regions of imagery data.

Advantageously, a single digital slide may have multiple scores associated with it, including scores for portions, regions, and the entire slide at the scanning resolution, as well as scores for portions, regions, and the entire slide at reduced intermediate resolutions all the way down to the smallest resolution thumbnail image of the entire slide (and portions and regions thereof).

Figure 3:
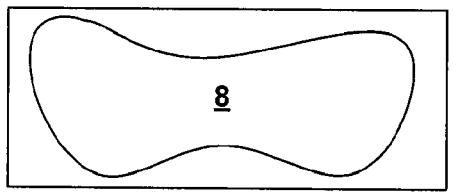
FIG. 3 is a block diagram illustrating an example digital slide with an overall score according to an embodiment of the present invention.
Figure 4:
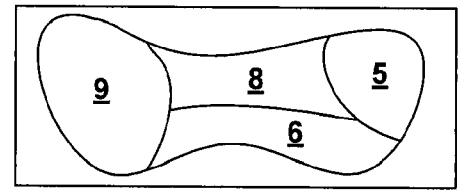
FIG. 4 is a block diagram illustrating an example digital slide with portions of the digital slide separately scored according to an embodiment of the present invention.

FIG. 3 is a block diagram illustrating an example digital slide with an overall score of 8 according to an embodiment of the present invention. FIG. 4 is a block diagram illustrating an example digital slide with regions of the digital slide separately scored according to an embodiment of the present invention. A first region has a score of 9, a second region has a score of 8, a third region has a score of 6 and a fourth region has a score of 5. There may be more or fewer regions that are separately scored.

Figure 5:
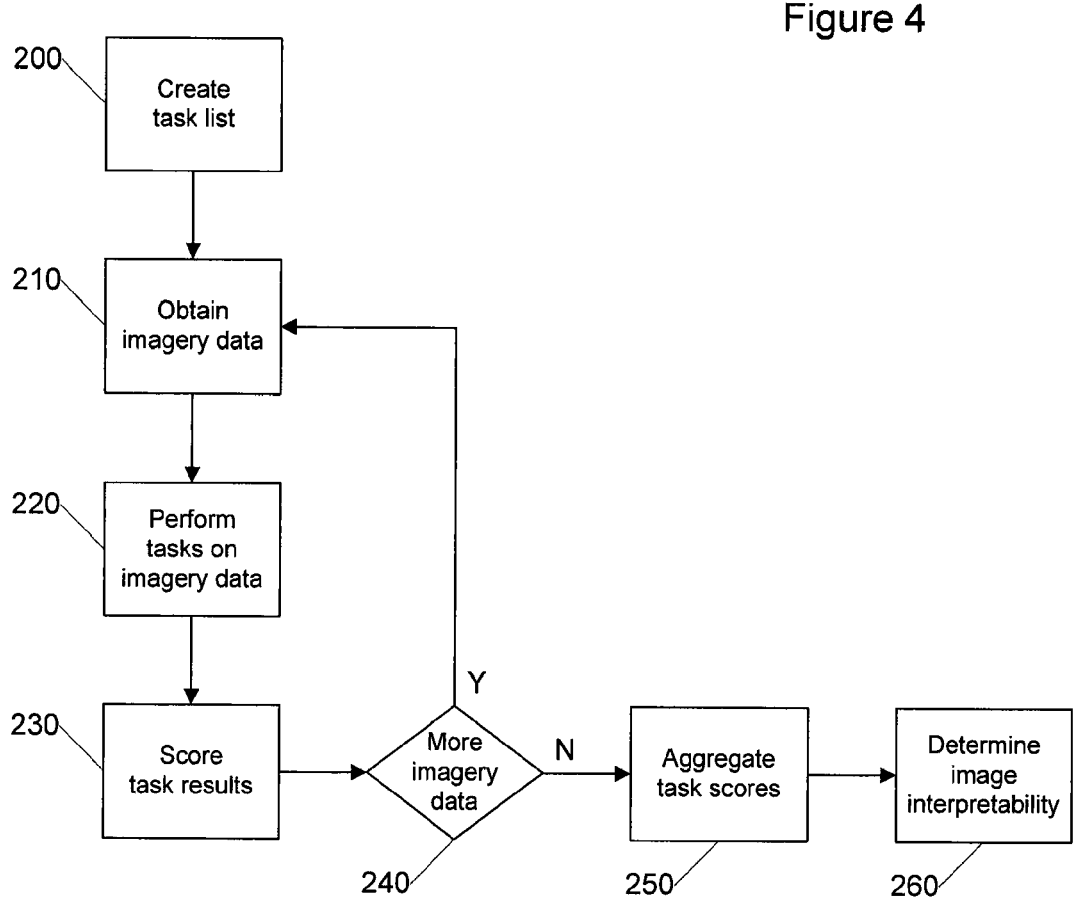
FIG. 5 is a flow diagram illustrating an example process for image interpretability assessment according to an embodiment of the present invention.

FIG. 5 is a flow diagram illustrating an example process for image interpretability assessment according to an embodiment of the present invention. The illustrated process can be carried out by a system such as previously described with respect to FIG. 1 or a server such as previously described with respect to FIG. 2. Initially, in step 200 the task list is created. The task list can be initially formed by a group of pathologists, an organization, a governmental entity or otherwise. Once initially formed, the task list is then created into the system so that it may be carried out in the context of image interpretability assessment. Next, in step 210 imagery data is obtained from a digital slide. Imagery data may be obtained from a local data storage area, directly from a scanning device, or from a remote scanning device or remote data storage area. In one embodiment, imagery data is obtained in manageable sized portions, a plurality of which combine to form a region. An entire digital slide may be made up of many portions and regions.

Once the imagery data is obtained, in step 220 the various tasks in the set of tasks required for the particular tissue type is performed on the imagery data. The set of tasks may be performed entirely by an analyst, partially by an analyst or not at all by an analyst. Similarly, the set of tasks may also be performed entirely by image processing algorithms, partially by image processing algorithms, or not at all by image processing algorithms. In certain cases, some tasks may be performed by an analyst while other tasks may be performed by image processing algorithms. Additionally, some tasks may be performed by both an analyst and an image processing algorithm to provide more robustness and also to corroborate the success or failure of performing the task on the imagery data.

While the tasks are being performed, a score for each task is recorded, as shown in step 230. The score can be a simple binary success or failure metric that is recorded. The score may also be a more sophisticated representation of success or failure, for example a percentage of success versus failure if the task was attempted to be performed multiple times. Next, in step 240, if there is more imagery data to be analyzed or if not enough imagery data has yet been analyzed to create a robust overall score for the digital slide, then the process loops back to step 210 where additional imagery data is obtained for analysis. However, if analysis of more imagery data is not needed, the process continues to step 250 where the individual task scores are aggregated to create an overall score for the digital slide. The scores may also be calculated with different level of complexity in the calculation to provide more granular and robust scoring results than simple aggregation may provide. Furthermore, the calculating of overall scores may be done for separate regions within the digital slide as well as for the entire digital slide. Finally, in step 260 the image interpretability is determined. In one embodiment, the image interpretability may be the same as the overall digital slide score, but it may alternatively be determined based on the overall score in combination with the various regional scores.

FIG. 6 is a block diagram illustrating an example image interpretability task list according to an embodiment of the present invention. Depending on the tissue type, there may be any number of tasks identified as part of the required set of tasks for diagnosing the particular tissue type.

FIG. 7 is a block diagram illustrating an example image interpretability rating scale according to an embodiment of the present invention. In the illustrated embodiment, there are ten separate levels of image interpretability such that a digital slide image (or region or portion) with a scale of zero is an image having the lowest image quality. In contrast, a digital slide image (or region or portion) with a scale of nine is an image having the highest image quality.

FIGS. 8-11 are block diagrams illustrating example image interpretability scores according to an embodiment of the present invention. As shown in the illustrated embodiment, binary (yes/no) scores from ten pathologists when viewing portions of imagery data at four different image qualities (A=best, D=worst) are recorded. FIG. 12 is a block diagram illustrating an example image interpretability scoring summary of the recorded scores from FIGS. 8-11.

Figures 14, 15:
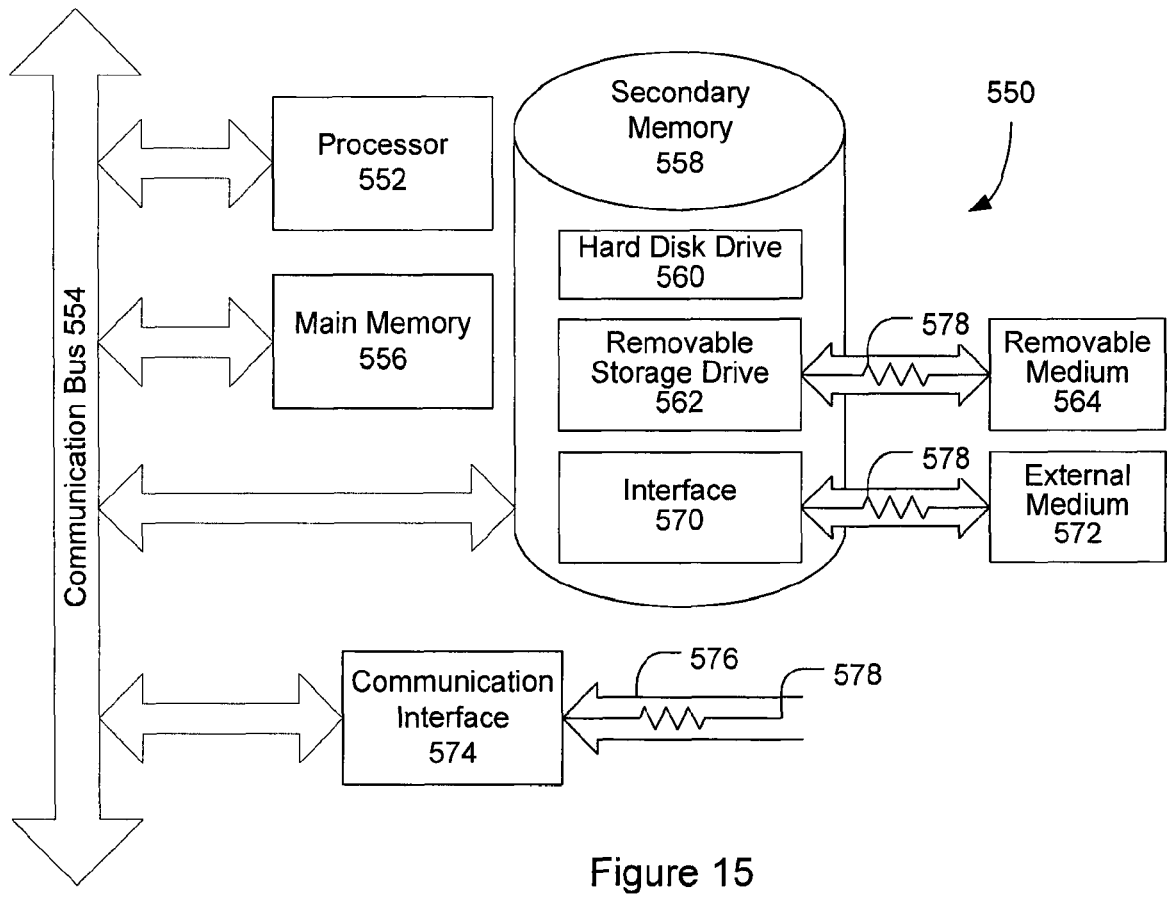
FIG. 14 is a block diagram illustrating an example ranking of image interpretability tasks against image interpretability according to an embodiment of the present invention.
FIG. 15 is a block diagram illustrating an example computer system that may be used in connection with various embodiments described herein.

FIG. 13 is a block diagram illustrating an example image interpretability task ranking according to the example shown in FIGS. 8-12. FIG. 14 is a block diagram illustrating an example ranking of tasks against image interpretability according to the example shown in FIGS. 8-12. As shown in the illustrated embodiment of FIGS. 13 and 14, task four was the easiest task to perform and is therefore relatively ranked as the least challenging and is associated with the lowest image quality. In contrast, task one was the most difficult task to perform and is therefore relatively ranked as the most challenging and is associated with the highest image quality. Otherwise stated, the more challenging the task that can be successfully performed on the imagery data, the higher the quality of the imagery data, and the higher the image interpretability score.

FIG. 15 is a block diagram illustrating an example computer system 550 that may be used in connection with various embodiments described herein. For example, the computer system 550 may be used in conjunction with the server or reviewer devices previously described with respect to FIG. 1. However, other computer systems and/or architectures may be used, as will be clear to those skilled in the art.

The computer system 550 preferably includes one or more processors, such as processor 552. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 552.

The processor 552 is preferably connected to a communication bus 554. The communication bus 554 may include a data channel for facilitating information transfer between storage and other peripheral components of the computer system 550. The communication bus 554 further may provide a set of signals used for communication with the processor 552, including a data bus, address bus, and control bus (not shown). The communication bus 554 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 550 preferably includes a main memory 556 and may also include a secondary memory 558. The main memory 556 provides storage of instructions and data for programs executing on the processor 552. The main memory 556 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 558 may optionally include a hard disk drive 560 and/or a removable storage drive 562, for example a floppy disk drive, a magnetic tape drive, a compact disc ("CD") drive, a digital versatile disc ("DVD") drive, etc. The removable storage drive 562 reads from and/or writes to a removable storage medium 564 in a well-known manner. Removable storage medium 564 may be, for example, a floppy disk, magnetic tape, CD, DVD, etc.

The removable storage medium 564 is preferably a computer readable medium having stored thereon computer executable code (i.e., software) and/or data. The computer software or data stored on the removable storage medium 564 is read into the computer system 550 as electrical communication signals 578.

In alternative embodiments, secondary memory 558 may include other similar means for allowing computer programs or other data or instructions to be loaded into the computer system 550. Such means may include, for example, an external storage medium 572 and an interface 570. Examples of external storage medium 572 may include an external hard disk drive or an external optical drive, or and external magneto-optical drive.

Other examples of secondary memory 558 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 572 and interfaces 570, which allow software and data to be transferred from the removable storage unit 572 to the computer system 550.

Computer system 550 may also include a communication interface 574. The communication interface 574 allows software and data to be transferred between computer system 550 and external devices (e.g. printers), networks, or information sources. For example, computer software or executable code may be transferred to computer system 550 from a network server via communication interface 574. Examples of communication interface 574 include a modem, a network interface card ("NIC"), a communications port, a PCMCIA slot and card, an infrared interface, and an IEEE 1394 fire-wire, just to name a few.

Communication interface 574 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 574 are generally in the form of electrical communication signals 578. These signals 578 are preferably provided to communication interface 574 via a communication channel 576. Communication channel 576 carries signals 578 and can be implemented using a variety of wired or wireless communication means including wire or cable, fiber optics, conventional phone line, cellular phone link, wireless data communication link, radio frequency (RF) link, or infrared link, just to name a few.

Computer executable code (i.e., computer programs or software) is stored in the main memory 556 and/or the secondary memory 558. Computer programs can also be received via communication interface 574 and stored in the main memory 556 and/or the secondary memory 558. Such computer programs, when executed, enable the computer system 550 to perform the various functions of the present invention as previously described.

In this description, the term "computer readable medium" is used to refer to any media used to provide computer executable code (e.g., software and computer programs) to the computer system 550. Examples of these media include main memory 556, secondary memory 558 (including hard disk drive 560, removable storage medium 564, and external storage medium 572), and any peripheral device communicatively coupled with communication interface 574 (including a network information server or other network device). These computer readable mediums are means for providing executable code, programming instructions, and software to the computer system 550.

In an embodiment that is implemented using software, the software may be stored on a computer readable medium and loaded into computer system 550 by way of removable storage drive 562, interface 570, or communication interface 574. In such an embodiment, the software is loaded into the computer system 550 in the form of electrical communication signals 578. The software, when executed by the processor 552, preferably causes the processor 552 to perform the inventive features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A system for comparing a digital slide image created by a first image capture device to a digital slide image created by a second image capture device comprising:
   a data storage area comprising a first digital slide image created by a first image capture device from a microscope slide sample and a second digital slide image created by a second image capture device from said microscope slide sample and one or more sets of image analysis tasks;
   an image module configured to obtain one or more portions of imagery data from the first digital slide image and the second digital slide image and provide said one or more portions of imagery data for performance of a set of image analysis tasks;
   a task performance module configured to manage the execution of a set of image analysis tasks on said one or more portions of imagery data from the first digital slide image and the second digital slide image and record one or more metrics related to the success of each image analysis task on said one or more portions of imagery data from the first digital slide image and the second digital slide image; and
   an image scoring module configured to analyze said success metrics and determine an image interpretability score for said one or more portions of imagery data from the first digital slide image and the second digital slide image upon which the set of image analysis tasks were executed and determine an overall image interpretability score for the first digital slide image and determine an overall image interpretability score for the second digital slide image, wherein said overall image interpretability scores provide a comparison of the first digital slide image and the second digital slide image.

2. The system of claim 1, wherein
   the image module is further configured to obtain and provide a plurality of portions of imagery data from the first and second digital slide images;
   the task performance module is further configured to manage the execution of the set of image analysis tasks on each of the plurality of portions of imagery data from the first and second digital slide images and record a metric related to the success of each image analysis task on each of the plurality of portions of imagery data, and
   the image scoring module is further configured to analyze the success metrics for a set of image analysis tasks and determine an image interpretability score for each of the plurality of portions of the imagery data from the first and second digital slide images upon which the set of image analysis tasks were executed and determine an overall image interpretability score for the first and second digital slide images.

3. The system of claim 2, wherein the image scoring module is further configured to determine an image interpretability score for one or more regions of the first and second digital slide images.

4. The system of claim 1, wherein the task performance module is further configured to present one or more portions of imagery data to an analyst and record the success or failure by the analyst in the performance of each task in the set of image analysis tasks.

5. The system of claim 1, wherein the task performance module is further configured to provide one or more portions of imagery data to an image analysis algorithm and record the success or failure by the image analysis algorithm in the performance of each task in the set of image analysis tasks.

6. The system of claim 1, wherein the task performance module is further configured to present one or more portions of imagery data to an analyst and record the success or failure by the analyst in the performance of one or more tasks in the set of image analysis tasks, and wherein the task performance module is further configured to provide said one or more portions of imagery data to an image analysis algorithm and record the success or failure by the image analysis algorithm in the performance of said one or more tasks in the set of image analysis tasks.

7. The system of claim 1, further comprising a task module configured to manage the one or more sets of image analysis tasks in the data storage area.

8. The system of claim 7, wherein the task module is configured for at least one of creation, deletion, and modification of the one or more sets of image analysis tasks.

9. A computer implemented method for determining image interpretability comprising:
   obtaining one or more portions of imagery data from a first digital slide image and a second digital slide image;
   executing of a set of image analysis tasks on said one or more portions of imagery data from the first digital slide image and the second digital slide image;
   recording one or more metrics related to the success of each image analysis task on said one or more portions of imagery data from the first digital slide image and the second digital slide image;
   analyzing said success metrics to determine an image interpretability score for said one or more portions of imagery data from the first digital slide image and the second digital slide image upon which the set of image analysis tasks were executed; and
   determining an overall image interpretability score for the first digital slide image and determining an overall image interpretability score for the second digital slide image, wherein said overall image interpretability scores provide a comparison of the first digital slide image and the second digital slide image.

10. The method of claim 9, wherein determining an overall image interpretability score further comprises calculating an image interpretability score for the entire digital slide image based on a plurality of image interpretability scores for a plurality of portions of imagery data from said digital slide image.

11. The method of claim 9, wherein determining an overall image interpretability score further comprises calculating an image interpretability score for a region of the digital slide image based on a plurality of image interpretability scores for a plurality of portions of imagery data from said region of the digital slide image.

12. The method of claim 11, wherein determining an overall image interpretability score further comprises calculating an image interpretability score for the entire digital slide image based on image interpretability scores for one or more regions of the digital slide image and image interpretability scores for one or more portions of imagery data from said digital slide image.

13. The method of claim 11, further comprising optimizing the image interpretability score for an entire digital slide image by analyzing a plurality of image interpretability scores for a plurality of regions of said digital slide.

14. The method of claim 11, further comprising optimizing the image interpretability score for a region of a digital slide image by analyzing a plurality of image interpretability scores for said region.

15. The method of claim 9, wherein the analyzing step further comprises presenting the portion of imagery data to an analyst.

16. The method of claim 9, wherein the analyzing step further comprises providing the portion of imagery data to an image analysis algorithm.

17. The method of claim 16, wherein the analyzing step further comprises presenting the portion of imagery data to a plurality of image analysis algorithms, wherein each image analysis algorithm executes one or more of the tasks in the set of image analysis tasks.

18. The method of claim 9, further comprising optimizing the image interpretability score for a portion of imagery data from a digital slide image by analyzing a plurality of image interpretability scores for said portion.

19. The method of claim 9, further comprising optimizing the image interpretability score for a region of imagery data from a digital slide image by analyzing a plurality of image interpretability scores for a plurality of portions of said digital slide.

* * * * *